United States Patent [19]

Hourahane

[11] Patent Number: 4,773,416

[45] Date of Patent: Sep. 27, 1988

[54] SURGERY IN HORSES

[76] Inventor: Donald H. Hourahane, Flat 3, Manor Court, Manor Park, Chiselhurst, Kent, United Kingdom

[21] Appl. No.: 10,774

[22] Filed: Feb. 4, 1987

[30] Foreign Application Priority Data

Feb. 7, 1986 [ZA] South Africa .................. 86/0929

[51] Int. Cl.$^4$ .............................................. A61B 17/00
[52] U.S. Cl. ................................. 128/303 R; 128/330; 604/164; 604/170; 623/13
[58] Field of Search ............... 206/363; 604/164, 170, 604/171, 364, 368; 128/303 R, 329 R, 330 R, 336, 340, 343, 759, 335.5

[56] References Cited

U.S. PATENT DOCUMENTS

| | | | |
|---|---|---|---|
| 3,106,483 | 10/1963 | Kline | 128/335.5 |
| 3,122,479 | 2/1964 | Smith | 128/335.5 |
| 3,438,524 | 2/1976 | Sparks et al. | 128/303 R |
| 3,883,901 | 5/1975 | Coquard et al. | 128/335.5 |
| 3,896,814 | 7/1975 | Vivien et al. | 128/335.5 |
| 4,498,902 | 2/1985 | Ash et al. | 604/164 |

OTHER PUBLICATIONS

Brown, et al—"Experimental and Clinical Investigations of the Use of Carbon Fiber Sutures in Equine Tendon Repair", JAVMA, vol. 182, No. 9, May 1, 1983, pp. 956-966.
Goodship, et al—"An Assessment of Filamentous Carbon Fibre for the Treatment of Tendon Injury in the Horse", The Veterinary Record, Mar. 8, 1980, pp. 217-221.
Nixon, et al—"Comparison of Carbon Fibre and Nylon Suture for Repair of Transected Flexor Tendons in the Horse", Equine Veterinary Journal (1984), 16(2), pp. 93-102.
Vaughan, et al—"Tendon Injuries in Horses Treated With Carbon Fibre Implants", Equine Veterinary Journal (1985) 17(1), pp. 45-50.
Valdez, et al—"Repair of Digital Flexor Tendon Lacerations in the Horse, Using Carbon Fiber Implants", JAVMA, vol. 177, No. 5, Sep. 1, 1980, pp. 427-435.
McCullagh, et al—"Tendon Injuries and Their Treatment in the Horse", The Veterinary Record, Jul. 21, 1979, pp. 54-57.

Primary Examiner—C. Fred Rosenbaum
Assistant Examiner—Mark F. Colosimo
Attorney, Agent, or Firm—Bernard, Rothwell & Brown

[57] ABSTRACT

The invention provides a method of surgery in horses for strengthening part of a horses flexo-tendon in a horse's leg. A cannula containing a probe projecting therefrom is inserted lengthwise into the tendon to intersect the part of the tendon to be strengthened, the probe forming a pocket in the tendon at the inner end of the cannula. The probe is removed from the cannula and an implant is inserted through the cannula so that its inner end is located and gripped in the pocket. The cannula is then removed to leave the implant located in the tendon and intersecting the part to be strengthened. The invention also provides a surgical kit comprising said cannula, probe and implant, and a thruster for thrusting the implant into the cannula; and the invention includes also the implant of the kit.

19 Claims, 4 Drawing Sheets

SURGERY IN HORSES

This invention relates, broadly, to surgery in horses. More particularly, the invention relates to a method of surgery for strengthening part of the flexo-tendon of a horse's leg in the vicinity of a horse's hoof, to a surgical kit for use in the method and to a surgical implant suitable for use in the method.

According to one aspect of the invention there is provided a method of surgery for strengthening part of a flexo-tendon in a horse's leg in the vicinity of the horse's hoof, which method comprises the steps of:

forming an incision in the horse's leg at a position between the horse's hoof and the part of the horse's flexo-tendon to be strengthened;

inserting a tubular cannula end-first into the incision and thrusting it end-first into the tendon so that it extends longitudinally along the interior of the tendon substantially parallel to the tendon and intersects the part of the tendon to be strengthened with one end of the cannula projecting out of the incision;

forming a pocket in the tendon longitudinally inwardly of the inner end of the cannula by means of a probe located in the hollow interior of the cannula and projecting from said inner end of the cannula, the probe and cannula being inserted simultaneously into the incision;

withdrawing the probe from the outwardly projecting end of the cannula to leave the pocket empty;

inserting a surgical implant comprising a bundle of fibres lengthwise into the outwardly projecting end of the cannula until the inner end of the bundle is located in the pocket, the length of the bundle being selected so that it is located entirely within the interior of the tendon;

withdrawing the cannula from the incision to cause the walls of the pocket in the tendon to clamp the bundle and to leave the bundle as a whole located entirely within the tendon and intersecting the part of the tendon to be strenthened; and closing the incision.

The incision may be made through the skin behind the horse's fetlock, by means of a blade whose plane is parallel to the fibres of the tendon, to extend into the tendon to a depth such that the inner end of the incision is at or adjacent the centre of the tendon, the cannula and probe initially being inserted into the incision until the inner end of the probe is at the inner end of the incision, and the cannula and probe then being manipulated until they are substantially parallel to the tendon, the cannula and probe then being thrust longitudinally along the tendon into a position intersecting said part of the tendon to be strengthened.

The method may include the preliminary step, before the incision is made, of clamping the horse's leg in a position such that the tendon to be strengthened is in an extended condition, under tension, approximating the extended condition occupied by the tendon when the horse's weight is being borne by that leg.

Clamping the horse's leg may comprise attaching a lever to a horse's hoof so that the lever extends away from the hoof along the front of the horse's leg, urging the lever towards the horse's leg to engage the front of the horse's fetlock to urge the fetlock rearwardly and to pull the hoof forwardly to extend said tendon, and attaching the lever to the horse's leg above the carpal/tarsal joint of the leg. In other words, when the lever has been attached to the horse's hoof to extend away from the hoof along the front of the horse's leg, the end of the lever remote from the hoof will thus be urged towards the front of the horse's leg, so that it engages the front or anterior side of the horse's fetlock, thereby to thrust and lever the fetlock rearwardly and, simultaneously, the hoof forwardly, to tension the flexo-tendon, after which the end of the lever remote from the hoof is attached, e.g. by strapping, to the horse's leg above the part of the leg to be strengthened.

Inserting the implant into the cannula may include inserting the inner end of the implant into the outwardly projecting end of the cannula, inserting an elongated thruster into the outwardly projecting end of the cannula so that the thruster engages a transverse shoulder on the insert at or adjacent the inner end of the insert, and thrusting the thruster into the cannula to cause the thruster to thrust the inner end of the implant into the pocket, the thruster being withdrawn from the incision after the cannula has been at least partially withdrawn from the incision. It is a matter of indifference whether or not the pocket remains open after withdrawal of the probe or collapses, as thrusting the inner end of the implant into the pocket by means of the thruster will in any event easily take place. The end of the implant and shoulder will at least partially be gripped by the walls of the pocket, and subsequent withdrawal of the cannula will permit collapse of the pocket sufficiently to grip the inner end of the implant firmly enough to hold it in position while the cannula and thruster are withdrawn fully. To assist in this gripping a lateral force may be applied to the outside of the horse's leg at a position aligned with and opposed to the pocket. As mentioned hereunder, the shoulder may be formed of resorbable material, such as one or more coils of suture material tied around the implant to form a collar which provides the shoulder.

Inserting the implant into the cannula may be directly from a tubular holder in which the implant is located, inserting the implant into the cannula acting simultaneously to withdraw the implant from the holder. This feature permits the implant to be kept in sterile conditions in a holder, and the end of the holder where the shoulder is located may be open to expose said end and shoulder for engagement only by the thruster, so that sterility of the implant is maintained.

The strengthening of the tendon may act to promote healing of damage to the tendon, the part of the tendon to be strengthened comprising a damaged part of the tendon. Naturally, instead, the surgery may be carried out for prophylactic instead of curative reasons, the part of the tendon to be strengthened comprising an undamaged part of the tendon, but one in which damage is anticipated. Thus, when a horse has damaged one of its tendons and that tendon is treated in accordance with the method of the present invention to promote healing, it is expected that the tendon of the opposite leg of the horse, undamaged, will often by treated to strengthen it, in anticipation of future damage, the damage to the tendon in the one leg indicating a predisposition towards damage in the tendon in the opposite leg.

As mentioned above, the implant is inserted so that it is located entirely within the interior of the tendon. This involves selecting the length of the implant, or cutting it prior to or during insertion, so that the whole of the implant is located within the interior of the tendon after insertion, and does not intersect any tissue interfaces such as the outer surface of the tendon, the sheath of the tendon, the skin, or the like. According to a particular procedure, inserting the implant into the cannula by means of the thruster may be initially to a position where the inner end of the implant is not fully in place in the pocket, the degree of insertion conveniently being determined with reference to reference markings or graduations on the thruster and on the cannula, at which stage the implant is cut to suitable length adjacent the outer end of the cannula, after which the thruster is thrust further until the inner end of the implant is fully home in the pocket.

The length of the cannula itself will be selected so that, for a typical case, after insertion of the cannula into the tendon, the outer end of the cannula projects out of the incision through the skin, by a spacing of about 150 mm or more. The cannula, probe, thruster, and as mentioned above, the implant, will typically be sterile before use, and any debris such as broken carbon fibres arising from the surgery will be confined to the vicinity of the outer end of the cannula, remote from the incision through the skin, so that the likelihood of such debris remaining in the incision, other than in the immediate proximity of the inserted implant, is substantially reduced. Preferably the length of the implant is selected so that the outer end of the implant, after insertion into the tendon, is no closer than say 15-20 mm to the surface of the tendon, being spaced from the outer surface of the tendon and tendon sheath. Sterility and the absence of debris, particularly at tissue interfaces, is thus promoted.

The eventual closing of the incision will be simple, the outer surface of the tendon being closed e.g. by a single stitch or suture, the sheath surrounding the tendon being closed similarly by a single stitch, as is the incision through the horse's skin.

Further according to the invention there is provided a surgical kit for use in the method described above, which kit comprises:

a tubular cannula;

an elongated probe slidable along the interior of the cannula and longer than the cannula;

a surgical implant comprising a bundle of fibres slidable along the interior of the cannula, the implant including a transverse shoulder at or adjacent one end of the bundle; and an elongated thruster slidable together with the bundle along the interior of the cannula, the thruster being longer than the cannula and having a width which prevents it from being slid past the shoulder in the interior of the cannula.

The cannula, probe and thruster may be of surgical steel construction, being straight, the probe having a head at one end thereof which prevents it from passing through the cannula, and the thruster having a point at one end thereof and a head at the opposite end thereof which prevents it from passing through the cannula. In use the ends of the probe and thruster having the heads, will be the outer ends thereof. The cannula, probe and thruster may be of substantially constant diameter, the probe being a sliding fit in the cannula, the cannula having an outer diameter of 4-5 mm, an inner diameter of 2-3 mm and a length of 250-300 mm, the cannula and probe having external graduations along their lengths, and the probe and thruster each being about 15-30 mm longer than the cannula. The fibres of the bundle may be carbon monofilament fibres, the fibres being 0.005-0.010 mm, e.g. 0.007 mm, in diameter and the bundle comprising 10,000-60,000 fibres, the shoulder being 2-4 mm from the adjacent end of the bundle and being resorbable. Instead, the fibres of the bundle may be biocompatible polymeric monofilament fibres, e.g. polyethylene fibres, the fibres being 0.010-0.025 mm in diameter and the bundle comprising 5,000-25,000 fibres, the shoulder being 2-4 mm from the adjacent end of the bundle and being resorbable. As mentioned above, the cannla and probe may be provided with one or more markings, such as spaced graduations extending in series along their outer surfaces, with reference to which a surgeon can judge the depth of insertion of the cannula into an incision, and the depth of insertion of the probe into the cannula, respectively. As also mentioned above, the shoulder is preferably resorbable, and is conveniently formed from several loops or coils of resorbable suture material coiled and tied securely around the end of the bundle to form a collar, and tied in a fashion such that it does not close off capillary spaces between the fibres of the bundle.

The kit may include a clamp for clamping a horse's hoof in a position which places the horse's flexo-tendon associated with the hoof in tension, the clamp comprising an elongated lever having a transverse bracket at one end thereof for engaging the bottom of a horse's hoof when the lever is attached to the horse's leg to extend along the anterior side thereof.

It will be appreciated that most of the items of the kit, such as the cannula, probe, thruster and clamp will be substantially indefinitely reusable. However, the implant itself will be left permanently in the horse's tendon, and is accordingly disposable.

The invention thus extends to a surgical implant suitable for use in accordance with the method of the invention and for forming part of the kit described above, which comprises a bundle of fibres and a collar around the bundle at or adjacent one end of the bundle whereby the fibres are held together. The collar may be of resorbable material, the fibres being carbon monofilament fibres, in which case the bundle may comprise 10,000-60,000 fibres of diameter 0.005-0.010 mm, the collar comprising a plurality of coils of suture material, located at 2-4 mm from the adjacent end of the bundle. Instead, the collar may be of resorbable material, the fibres being biocompatible polymeric monofilament fibres, in which case the bundle may comprise 5,000-25,000 fibres of diameter 0.010-0.025 mm, the collar comprising a plurality of coils of suture material, located 2-4 mm from the adjacent end of the bundle. The implant may be provided in sterile form in a tubular holder, the fibres of the implant being impregnated with gelatine, and the holder being contained in a sealed package. This tubular holder may be open ended, being for example a plastics tube open at both ends, and the gelatine or like biocompatible material impregnated therein will act to lubricate the implant, to hold its fibres together and to close off the capillary spaces between the fibres, to keep them clean. The end of the holder in which the collar is located may be obliquely sectioned to provide an elliptical opening which exposes the collar.

The implant may comprise dissimilar metals, dissimmilar in electrochemical potential, e.g. platinum and silver, one at or adjacent the collar and the other spaced from the collar, which metals can create or promote the existence of a galvanic field in the tendon adjacent the implant to promote strengthening of the tendon. Such metals may be in any convenient form, and they may be deposited on the fibres, e.g. as a coating or by plating.

The clamp may comprise a lever or bar, e.g. of metal, the bracket being formed by a bent end portion of the bar. Attachment of the clamp to the hoof and leg of the horse may be by lashing with suitable lashing material.

The invention will now be described, by way of example, with reference to the accompanying diagrammatic drawings, in which.

Figure 8A:
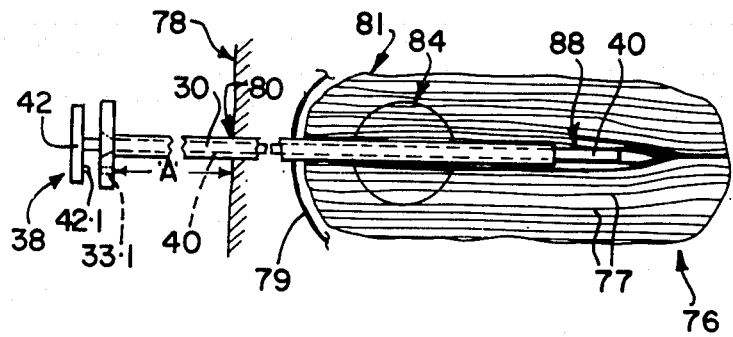
Figure 8B:
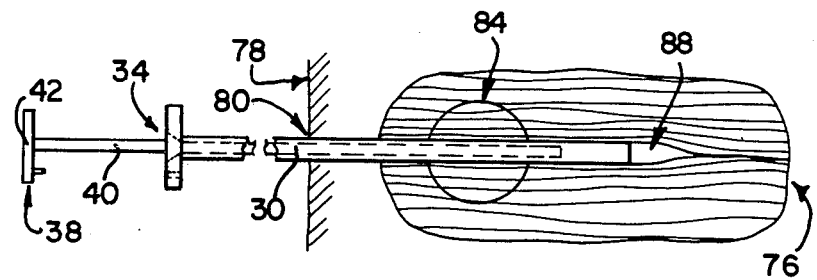
Figure 8C:
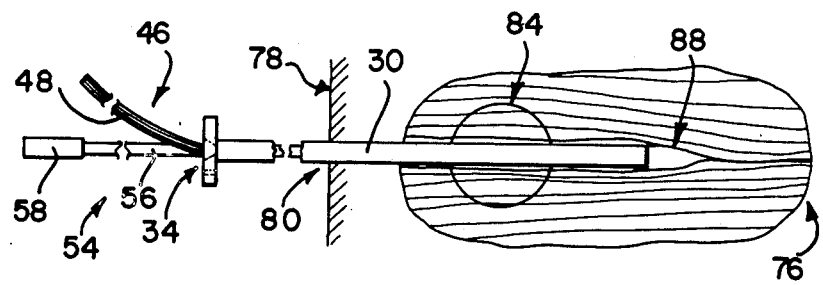
Figure 8D:
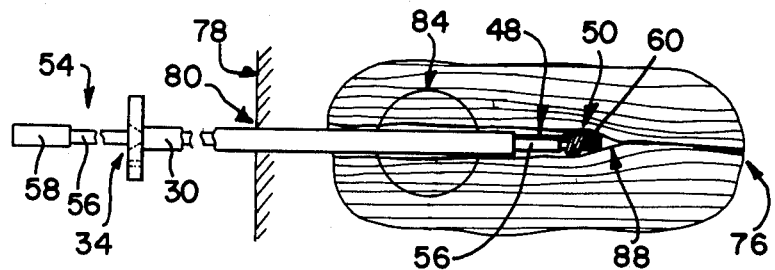
Figure 8E:
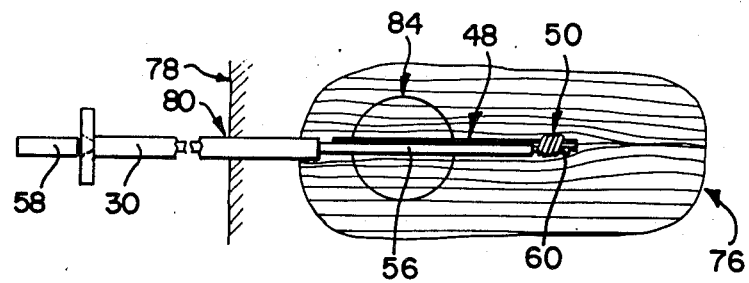
Figure 8F:
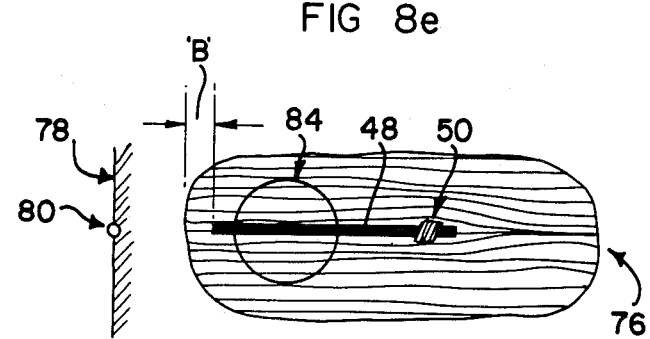
Figure 9:
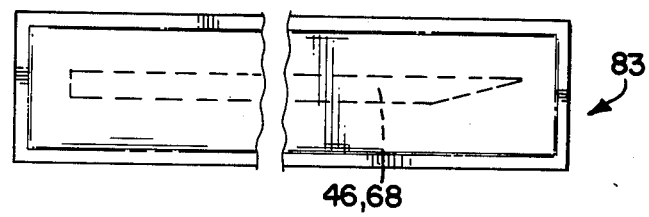

FIGS. 8(a) to 8(f) show schematic cut away partial side elevations of a horse's leg undergoing a surgical operation in accordance with the method of the present invention; and FIG. 9 shows the implant of the kit in its holder and package.

Figure 1:
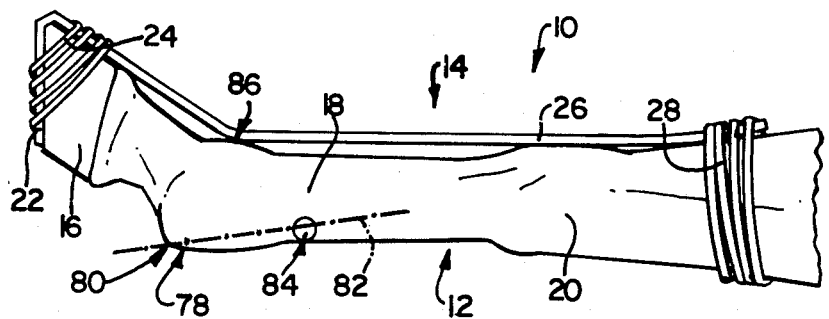
FIG. 1 shows a schematic side elevation of a horse's foreleg clamped in a clamp forming part of the kit of the present invention.

In FIG. 1 of the drawings, reference numeral 10 generally designates a schematic side elevation of a horse's foreleg 12 clamped in a clamp 14 forming part of the kit of the present invention. The part of the foreleg 12 shown comprises the hoof 16, fetlock 18 and hock 20.

The clamp 14 comprises a bracket 22 shown engaging the hoof 16 and lashed thereto by lashing 24. The bracket 22 is integral with and forms a bent end of an elongated metal lever 26 which extend up the anterior side of the fetlock 18 to above the hock 20, where it is lashed to the horse's leg 12 above the hock 20 by means of lashing 28.

Figure 2:
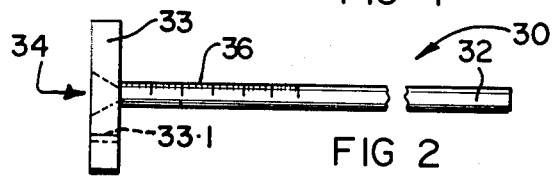
FIG. 2 shows a side elevation of a cannula forming part of said kit.

Turning to FIG. 2 of the drawings, reference numeral 30 generally designates a cannula forming part of the kit in accordance with the invention. The cannula 30 comprises a elongated straight surgical steel tube 32 having a T-bar head 33 at one end thereof which is countersunk to provide a mouth 34, the tube being provided with graduation marks along its length, some of which are shown at 36. The cannula is open at both ends. Typical dimensions for the cannula will be an inner diameter of 2½ mm, an outer diameter of 4½ mm, and a length of 275 mm.

Figure 3:
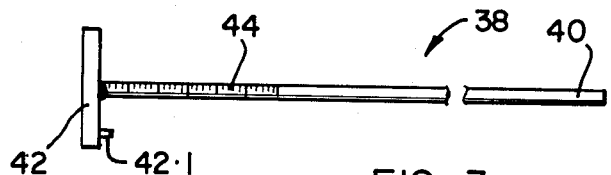
FIG. 3 shows a side elevation of a probe forming part of said kit.

Turning to FIG. 3, reference numeral 38 generally designates a probe forming part of the kit of the invention. The probe 38 comprises an elongated shank 40 in the form of a surgical steel rod, having a T-bar head or stop 42 at one end thereof, the head 42 having a projection 42.1 receivable in a passage 33.1 in the head 33 of the cannula 30, to prevent relative rotation between the cannula 30 and probe 38. The rod 40 is also provided with graduation markings, some of which are shown at 44, along its length. The shank 40 of the probe 38 is a sliding fit in the tube 32 of the cannula 30, the shank 40 being say 25 mm longer than said tube 32. The end of shank 40 remote from the head 42 is bullet-nosed and rounded, or is chisel-shaped in the fashion of a screwdriver.

Figure 4:
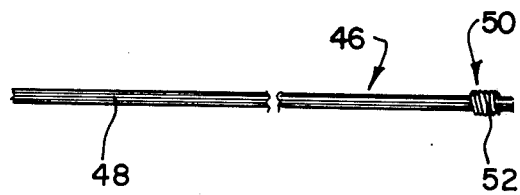
FIG. 4 shows a side elevation of an implant forming part of said kit.

In FIG. 4 a surgical implant forming part of the kit of the invention is generally designated 46. The implant shown comprises a bundle 48 of carbon monofilament fibres, and is provided at its one end with a circumferential shoulder or collar 50 located 2 mm from the adjacent end of the bundle and formed by a plurality of coils 52 of resorbable suture material looped around the bundle 48 and tied firmly in position. The implant 46 in turn will typically be somewhat shorter than the tube 32 of the cannula 30, and will comprise 50,000 fibres of diameter 0.007 mm.

Figure 5:
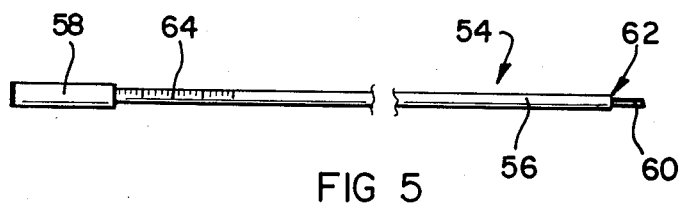
FIG. 5 shows a side elevation of a thruster forming part of said kit.

In FIG. 5, a thruster 54 forming part of the kit of the invention is shown. The thruster comprises a shank 56 in the form of a surgical steel rod, having a head 58 at one end thereof, and its opposite end a narrowed portion 60 of reduced diameter which forms a point for the thruster, which emerges from a shoulder 62 at the end of the thruster. The shank 56 of the thruster is provided with graduation markings, along its length, some of which are shown at 64. The thruster 54 is somewhat longer than the probe 38, and can fit, together with the implant bundle 48, slidably into the cannula 30.

Figure 6:
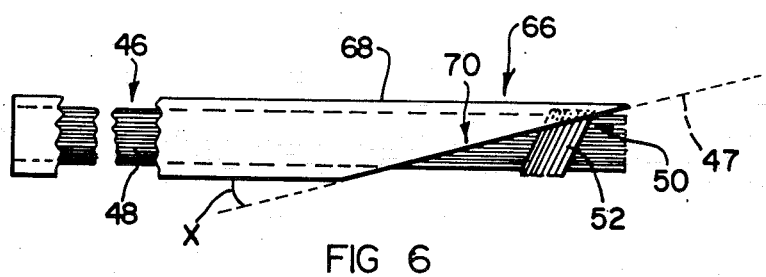
FIG. 6 shows a partial side elevation of part of the implant of FIG. 4 in a sheath or tubular holder.
Figure 7:
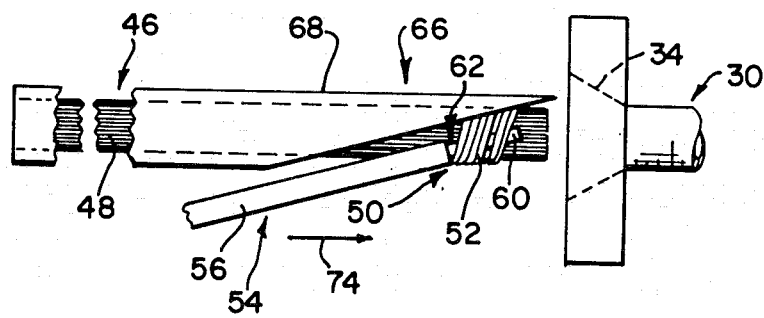
FIG. 7 shows the view of FIG. 6 with the sheath in use.

Turning now to FIGS. 6 and 7, reference numeral 66 generally designates the implant 46 of FIG. 4 located in a synthetic plastics tubular open-ended sheath or holder 68. Unless otherwise specified, the same reference numerals refer to the same parts as in FIGS. 2, 4 and 5, the assembly in FIG. 7 being shown in operative association with the cannula 30 of FIG. 2 and the thruster 54 of FIG. 5.

The sheath 68 is closed before use in an air-tight foil package or the like, and is provided with a tapered open end at 70 (FIG. 6). The collar is located at said tapered end 70, the opposite end being open but not tapered. The tapered end is provided by an oblique section along plane 47 through the plastics tube from which the sheath is formed, at an acute angle X to the axis of the tube. In this regard it is to be noted that the fibres of the bundle 48, to keep the fibres together and sterile, are coated with gelatine.

In FIG. 7, the sheat 68 is shown with its tapered end axially aligned with the mouth 34 of the cannula 30, and with the thruster 54 operatively thrust into position, with its point 60 passing under the coils 52 of the collar 50, between said coils and the bundle 48. The shoulder 62 abuts the shoulder provided by the coils 52 of the collar 50, in a position such that the thruster can be used to thrust the implant 46 in the direction of arrow 74 out of the sheath 68 and into the cannula 30 via its mouth 34.

In FIGS. 8(a) to 8(f), the same reference numerals are used, where appropriate, as in FIGS. 1 to 7, unless otherwise specified. Part of one of the flexo-tendons of the fetlock 18 of the leg 12 of FIG. 1 is shown schematically at 76, being made up of a plurality of essentially parallel tendon fibres 77, as shown. The skin of the horse's fetlock is shown at 78, wherein an incision has been formed at 80 (see also FIG. 1). Part of the sheath of the tendon 76 is shown at 79, enclosing the outer surface 81 of the tendon 76 (FIG. 8(a)).

In FIG. 9 the implant 46 in its sheath or holder 68 is shown in a foil package 83.

In accordance with the method of the invention, the kit is used to perform a surgical operation which acts to improve the blood supply to the tendon, thereby to strengthen and/or promote the healing of damage to the flexo-tendon 76 in the horse's leg 12. In this regard the general location of the flexo-tendon is indicated by the chain-dotted line 82 in FIG. 1, and the part to be strengthened or which is damaged is indicated by a circle 84.

The horse is prepared for the operation by being suitably anaesthetized and supported, after which its leg 12 is clamped in its extended condition as shown in FIG. 1, by means of the clamp 14. To do this, the bracket 22 of the clamp 14 is engaged with the bottom of the hoof 16, and is lashed thereto with the lashing 24. The lever 26 is then levered rearwardly engaging the fetlock 18 at 86 to urge the fetlock rearwardly and to lever the hoof fowardly, thereby to extend the leg and place the tendon 76, 82 under tension, after which the opposite end of the lever 26 is lashed to the leg 12 above the hock 20 by means of the lashing 28.

Figure 1A:
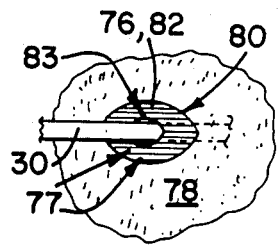
FIG. 1(a) shows a detail of FIG. 1.

An incision, typically about 25 mm in length, is then made at a suitable position as shown at 80 in FIG. 1, below the part 84, at the rear or posterior of the fetlock 18 proximal to the annular ligament of the horse and more or less aligned with the tendon 76, 82. This incision is made inwardly, proximal to the fetlock 18, and into the tendon 76, 82 to a depth whereby the bottom or inner end of the incision is located centrally in the interior of the tendon 76, 82. The incision is a slit whose plane is substantially parallel to the fibres of the tendon, the mouth of the incision at 80 being a slit which extends longitudinally along the leg. The incision is made by a blade, e.g. that of a scalpel, whose plane is substantially paralell to the fibres of the tendon, to keep the fibre damage to a minimum. In this regard it will be noted, with reference to FIG. 1(a), that the incision 80 through the skin 78 is shown, with the skin pulled back at the incision 80 to expose the fibres 77 of the tendon 76, 82. The incision through the tendon 76, 82 is shown at 83, with the cannula 30 projecting therethrough.

The cannula 30, in a sterile condition and with a sterile probe 38 inside it, is the inserted into the incision, to form an assembly whose end remote from the mouth 34 forms its front or leading end, the head 42 of the probe 38 being at the end of the cannula having the head 33 and mouth 34. When said front or leading end is at the bottom of the incision the assembly is manipulated in the incision, typically by levering it by about 70° about its inner end, so that the assembly is aligned more or less parallel with the longitudinal direction of the tendon as shown by 82 in FIG. 1. The assembly comprising the cannula 30 and probe 38 is then thrust longitudinally along the interior of said tendon, so that it intersects the part 84. The T-bar heads 33 and 42.1 and of the cannula 30 and probe 38, which engage via the projection 42 aid passage 33.1 to prevent relative rotation between the cannula 30 and probe 38, aid in this manipulation, and permit the assembly to clear the fetlock 18.

The cannula 30 is thrust in to a depth which is judged by the surgeon to be sufficient appropriately to intersect the part 84 of the tendon and to project past said zone of damage, the markings 36 being used to judge this depth. The probe 38 is thrust fully into the cannula 30, so that its head 42 abuts the head 33. The situation immediately after the assembly has been thrust into position is shown in FIG. 8(a), from which it will be apparent that the inner end of the shank 40 of the probe 38 projects out of the end of the tube 30 of the cannula remote from the mouth 34, into a pocket 88 (best seen in FIG. 8(b)) formed there by said end of the shank 40 of the probe 38. At this stage the shank is removed, leaving the pocket 88 at the inner end of the cannula 30, FIG. 8(b) showing the situation during removal of the probe 38 from the cannula 30. The outer end and head 33 are spaced by a spacing A (FIG. 8(a)) of about 150 mm from the skin at the incision 80. Removal of the probe 38 tends to cause the pocket 88 to collapse due to suction.

Turning now to FIG. 8(c) and FIG. 7, the situation is shown where the probe 38 has been removed from the cannula 30, and insertion of the implant 46 is taking place.

In FIG. 7, as mentioned above, the sheath 68 is shown removed from its foil package 83, to expose the end of the implant 46 having the collar 50 at the tapered end 70 of the sheath 68. The implant 46 is about to be inserted into the mouth 34 of the cannula 30, by means of the thruster 54, the point 60 of the thruster 54 having been inserted under the coils of suture material 52 forming the collar 50. Immediately before the implant is inserted, antibiotic is optionally injected into the sheath via its open end opposite the end 70, which antibiotic impregnates the gelatine coating of the fibres of the implant.

In FIG. 8(c), the thrusting the implant 46 into the cannula 30 has progressed somewhat, and the thruster 54 is shown with its shank or rod 56 thrust into the mouth 54 of the cannula 30, taking the implant 46 with it.

In FIG. 8(d) the thrusting step is shown completed, with the point 60 and adjacent end of the shank 56 of the thruster 54, and the adjacent end of the bundle 48 of the implant 46 with the collar 50, fully in position in the blind end of the pocket 88.

With the thruster 54 and implant 46 in this position, the cannula 30 is then partially withdrawn from the tendon 76 via the incision at 80. In this regard the cannula 30 is shown partially withdrawn in FIG. 8(e). The natural tendency of the fibres of the tendon 76 to close the pocket 88 clamps the collar 50 and adjacent end of the bundle 48 of the implant 46 sufficiently, to prevent withdrawal of the implant together with the cannula 30, the thruster 54 also serving to prevent withdrawal of the implant. The thruster 54 is then withdrawn from the incision, followed by the cannula. As the cannula 30 is withdrawn progressively, progressively more engagement takes place between the fibres of the tendon 76 and the bundle 48, holding the implant progressively more securely in position.

In this regard it should be noted that, at a suitable stage during insertion of the implant, for example the stage shown in FIG. 8(c), the bundle 48 may be cut adjacent the mouth 34 of the cannula 30, so that the bundle inserted into the tendon will be of a suitable length. Naturally, this cutting may be effected before insertion of the bundle into the cannula 30, or an implant having an bundle 48 of a suitable length may be selected initially, so that it does not require cutting. Although the implant is shown removed from the sheath 68 in FIG. 8(c) for clarity of illustration, when cutting of the bundle is required, the sheath is preferably kept around the bundle in position aligned with the mouth of the cannula, so that cutting may be effected while the bundle is inside the sheath. The sheath and bundle are cut together, the walls of the sheath acting to compress and grip the bundle, and hold its fibres together while it is being cut. The cutting will be such that the outer or trailing end of the bundle will be spaced from the incision through surface 81 of the tendon 76 by a spacing B (FIG. 8(f)).

When the cannula 30 has been withdrawn sufficiently as shown in FIG. 8(e), the thruster 54 may be withdrawn from the incision, followed by full withdrawal of the cannula, to leave the situation shown in FIG. 8(f). At that stage, the incision in the skin 78 at 80 may be closed by a single stitch, after, if desired, similarly closing the opening formed in the surface 81 of the tendon 76 by means of a single stitch, and closing the sheath 79 of the tendon with a single stitch.

As a refinement, the implant 46 may include platinum and silver e.g. plated or coated by vacuum deposition on the fibres, platinum being located at or adjacent the collar 50, and silver located at a position spaced from the collar 50 and platinum, on the bundle 48. These metals can set up a galvanic field in it vicinity of the part 84 of the tendon, which may promote rapid healing and/or tissue ingrowth and strengthening as described hereunder.

In the tendon 76, the implant 46 performs the function of promoting blood flow between one side of the part 84 of the tendon, and the other side of said part 84. In the absence of the implant, there is a danger that scarring and other damage in the part 84 may prevent or reduce blood flow from above the part 84, to positions below the part 84, which positions below the part 84 are in danger of suffering from necrosis. The implant, however, by means of capillary action between the fibres of the bundle 48, promotes good blood flow, rapid healing and strengthening, and encourages the development of new blood vessels. The galvanic action of the platinum and silver further promotes rapid healing and/or strengthening.

It is important to emphasise that the implant does not mechanically strengthen or reinforce the tendon immediately after it is inserted, its primary functions being to promote blood flow and to provide for tissue ingrowth in the implant and the production of additional collagen fibre formation and blood vessels such as capillaries. Only after tissue ingrowth has taken place can the implant bear any tensile load whatsoever, and this tensile load is in fact not relied upon to obtain the advantages of the invention.

The primary advantage of the invention, is that is provides a simply used kit and surgical method, for the rapid and substantially trauma-free insertion of the implant 46 into its desired operative position. Once the leg has been clamped by the clamp 14, the operation need take no longer than a few minutes, and involves the formation of a relatively small incision, followed by a minimal stitching. Small openings are made through the skin, the sheath around the tendon, and the surface of the tendon itself, thus reducing the likelihood of undesirable adhesions. Retaining the implant in the sheath 68 promotes a sterile conditions, and the packet 83 need not be opened no more than a few seconds before the implant 46 is inserted into position.

Furthermore, as mentioned above, and as shown e.g. in FIGS. 8(a) and 8(f), the outer end of the cannula and its head in use are spaced by a spacing A of about 150 mm from the incision and the ends of the carbon fibres are spaced by a spacing B of about 15–20 mm from the outer surface 81 and sheath 79 of the tendon. This means that, when a sterile kit is used, danger of infection is kept remote from the incision and debris formation (principally broken carbon fibres) is also kept away from the incision, at the mouth of the cannula. The chance that debris will be left in the incision through the skin, the incision through the tendon surface or in the tendon sheath is reduced, and the bundle itself is spaced from the tendon sheath 81 or the sheath 79.

I claim:

1. A method of surgery for strengthening part of a flexo-tendon in a horse's leg in the vicinity of the horse's hoof, which method comprises the steps of:
   forming an incision in the horse's leg at a position between the horse's hoof and the part of the horse's flexo-tendon to be strengthened;
   inserting a tubular cannula end-first into the incision and thrusting it end-first into the tendon so that it extends longitudinally along the interior of the tendon in a direction away from the horse's hoof and substantially parallel to the tendon and intersects the part of the tendon to be strengthened with one end of the cannula projecting out of the incision;
   forming a pocket in the tendon longitudinally inwardly of the inner end of the cannula by means of a probe located in the hollow interior of the cannula and projecting from said inner end of the cannula, the probe and cannula being inserted simultaneously into the incision;
   withdrawing the probe from the outwardly projecting end of the cannula to leave the pocket empty;
   inserting a surgical implant comprising a bundle of fibres lengthwise into the outwardly projecting end of the cannula until the inner end of the bundle is located in the pocket, the length of the bundle being selected so that it is located entirely within the interior of the tendon;
   withdrawing the cannula from the incision to cause the walls of the pocket in the tendon to clamp the bundle and to leave the bundle as a whole located entirely within the tendon and intersecting the part of the tendon to be strengthened; and
   closing the incision.

2. A method as claimed in claim 1, in which the incision is made through the skin behind the horse's fetlock, by means of a blade whose plane is parallel to the fibres of the tendon, to extend into the tendon, to a depth such that the inner end of the incision is at or adjacent the centre of the tendon, the cannula and probe initially being inserted into the incision until the inner end of the probe is at the inner end of the incision, and the cannula and the probe then being manipulated until they are substantially parallel to the tendon, the cannula and probe then being thrust longitudinally along the tendon into a position intersecting said part of the tendon to be strengthened.

3. A method as claimed in claim 1, which includes the preliminary step, before the incision is made, of clamping the horse's leg in a position such that the tendon to be strengthened is in an extended condition, under tension, approximating the extended condition occupied by the tendon when the horse's weight is being borne by that leg.

4. A method as claimed in claim 3, in which clamping the horse's leg comprises attaching a lever to the horse's hoof so that the lever extends away from the hoof along the front of the horse's leg, urging the lever towards the horse's leg to engage the front of the horse's fetlock to urge the fetlock rearwardly and to pull the hoof forwardly to extend said tendon, and attaching the lever to the horse's leg above the carpal/tarsal joint of the leg.

5. A method as claimed in claim 1, in which inserting the implant into the cannula includes inserting the inner end of the implant into the outwardly projecting end of the cannula, inserting an elongated thruster into the outwardly projecting end of the cannula so that the thruster engages a transverse shoulder on the insert at or adjacent the inner end of the insert, and thrusting the thruster into the cannula to cause the thruster to thrust the inner end of the implant into the pocket, the thruster being withdrawn from the incision after the cannula has been at least partially withdrawn from the incision.

6. A method as claimed in claim 5, in which the implant is inserted into the cannula directly from a tubular holder in which the implant is located, inserting the implant into the cannula acting simultaneously to withdraw the implant from the holder.

7. A method as claimed in claim 1, in which strengthening the tendon acts to promote healing of damage to the tendon, the part of the tendon to be strengthened comprising a damaged part of the tendon.

8. A surgical kit for carrying out the method of claim 1, which kit comprises:
   a tubular cannula;
   an elongated probe slidable along the interior of the cannula and longer than the cannula;
   a surgical implant comprising a bundle of fibres slidable along the interior of the cannula, the implant including a transverse shoulder at or adjacent one end of the bundle; and
   an elongated thruster slidable together with the bundle along the interior of the cannula, the thruster being longer than the cannula and having a width which prevents it from being slid past the transverse shoulder of the implant when the implant is in the interior of the cannula.

9. A kit as claimed in claim 8, in which the cannula, probe and thruster are of surgical steel construction and are straight, the probe having a head at one end thereof which prevents it from passing through the cannula, and the thruster having a point at the one end thereof and a head at the opposite end thereof which prevents it from passing through the cannula.

10. A kit as claimed in claim 9, in which the cannula, probe and thruster are of substantially constant diameter, the probe being a sliding fit in the cannula, the cannula having an outer diameter of 4–5 mm, an inner diameter of 2–3 mm and a length of 250–300 mm, the cannula and probe having external graduations along their lengths, and the probe and thruster each being about 15–30 mm longer than the cannula.

11. A kit as claimed in claim 8, in which the fibres of the bundle are carbon monofilament fibres, the fibres being 0.005–0.010 mm in diameter and the bundle comprising 10,000–60,000 fibres, the shoulder being 2–4 mm from the adjacent end of the bundle and being resorbable.

12. A kit as claimed in claim 8, in which the fibres of the bundle are biocompatible polymeric monofilament fibres, the fibres being 0.010—0.010 mm in diameter and the bundle comprising 5,000–25,000 fibres, the shoulder being 2–4 mm from the adjacent end of the bundle and being resorbable.

13. A kit as claimed in claim 8, which includes a clamp for clamping a horse's hoof in a position which places the horse's flexo-tendon associated with that hoof in tension, the clamp comprising an elongated lever having a transverse bracket at one end thereof for engaging the bottom of a horse's hoof when the lever is attached to the horse's leg to extend along the anterior side thereof.

14. A surgical implant for use as part of the kit of claim 8, which implant comprises a bundle of fibres and a collar around the bundle at or adjacent one end of the bundle whereby the fibres are held together, the collar forming a transverse shoulder at or adjacent said one end of the bundle for engagement by the thruster of the kit when the implant is in the interior of the cannula of the kit, to permit the implant to be slid along the interior of the cannula by means of the thruster.

15. An implant as claimed in claim 14, in which the collar is of resorbable material and the fibres are carbon monofilament fibres.

16. An implant as claimed in claim 15, in which the bundle comprises 10,000–60,000 fibres of diameter 0.005–0.010 mm and the collar comprises a plurality of coils of surgical suturing thread, located 2–4 mm from the end of the bundle.

17. An implant as claimed in claim 14, in which the collar is of resorbable material and the fibres are biocompatible polymeric monofilament fibres.

18. An implant as claimed in claim 17, in which the bundle comprises 5,000–25,000 fibres of diameter 0.010–0.025 mm and the collar comprises a plurality of coils of surgical suturing thread, located 2–4 mm from the end of the bundle.

19. An implant as claimed in claim 14, in which the implant is provided in sterile form in a tubular holder, the fibres of the implant being coated with gelatine and the holder being contained in a sealed package.

* * * * *

UNITED STATES PATENT AND TRADEMARK OFFICE
CERTIFICATE OF CORRECTION

PATENT NO. : 4,773,416

DATED : September 27, 1988

INVENTOR(S) : Donald H. Hourahane

It is certified that error appears in the above-identified patent and that said Letters Patent is hereby corrected as shown below:

Column 4, line 8, "cannla" should be --cannula--.

Column 5, line 38, "extend" should be --extends--.

Column 6, line 15, after "and" insert --at--.

Column 7, line 9, after "rearwardly" insert --,--.

Column 8, line 60, after "bundle" insert --,--.

Column 9, line 37, "in" should be --into--;

line 55, delete "not".

Column 10, line 2, "sheath" (first occurrence) should be --surface--.

Column 12, line 7, "0.010-0.010" should be --0.010-0.025--.

Signed and Sealed this
Twenty-seventh Day of February, 1990

Attest:

JEFFREY M. SAMUELS

Attesting Officer      Acting Commissioner of Patents and Trademarks